United States Patent
Tanifuji

(10) Patent No.: US 7,429,246 B2
(45) Date of Patent: Sep. 30, 2008

(54) ORGANISM INFORMATION MEASURING DEVICE

(75) Inventor: Norio Tanifuji, Chiba (JP)

(73) Assignee: Seiko Instruments Inc. (JP)

( * ) Notice: Subject to any disclaimer, the term of this patent is extended or adjusted under 35 U.S.C. 154(b) by 476 days.

(21) Appl. No.: 11/121,261

(22) Filed: May 3, 2005

(65) Prior Publication Data

US 2005/0251058 A1 Nov. 10, 2005

(30) Foreign Application Priority Data

May 7, 2004 (JP) ............................. 2004-138101

(51) Int. Cl.
*A61B 5/02* (2006.01)
(52) U.S. Cl. ..................................... 600/500
(58) Field of Classification Search .................. 600/500
See application file for complete search history.

(56) References Cited

U.S. PATENT DOCUMENTS 5,960,367 A * 9/1999 Kita ............................ 455/567
6,893,395 B1 * 5/2005 Kraus et al. .................. 600/300

FOREIGN PATENT DOCUMENTS

JP 07017202 3/1995

* cited by examiner

*Primary Examiner*—Charles A. Marmor, II
*Assistant Examiner*—Christian Y Jang
(74) *Attorney, Agent, or Firm*—Adams & Wilks

(57) ABSTRACT

An organism information measuring device has a reception unit that receives organism information generated cyclically. A detection unit detects and transmits the organism information to the reception unit by electromagnetic induction. A notification unit provides notification of receipt of the organism information by the reception unit while generating electromagnetic noise. A control circuit controls the reception unit to stop a reception operation for a predetermined period less than a cycle in which the organism information is generated and controls the notification unit to provide notification of receipt by the reception unit of the organism information transmitted by the detection unit while the reception operation of the reception unit is stopped. In this manner, interference between electromagnetic noise generated by the notification unit and an electromagnetic induction signal transmitted by the detection unit is prevented.

23 Claims, 6 Drawing Sheets

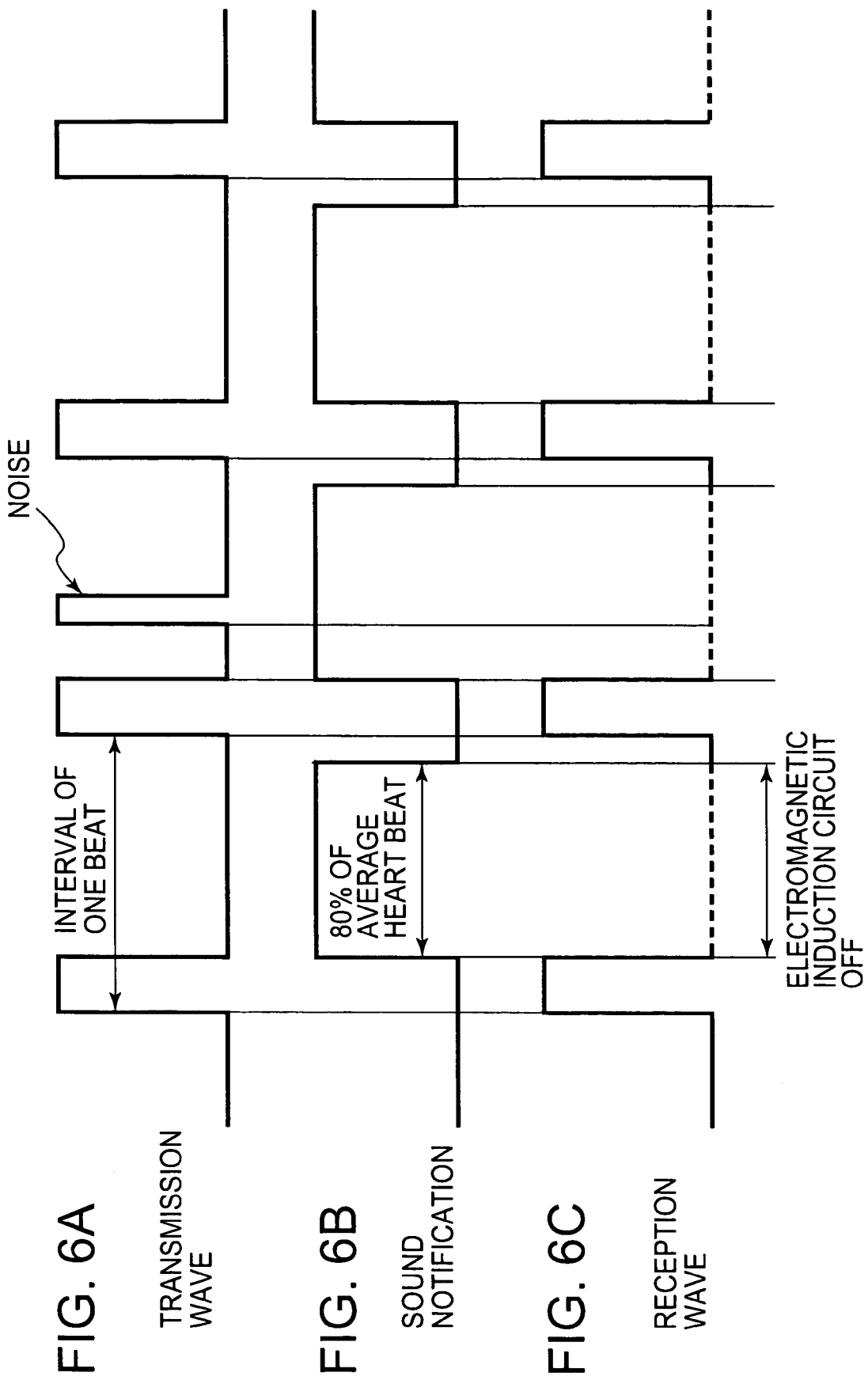

ORGANISM INFORMATION MEASURING DEVICE

BACKGROUND OF THE INVENTION

1. Field of the Invention

The present invention relates to an organism information measuring device which measures an organism information such as heart beat.

2. Description of the Prior Art

There has been developed an organism information measuring device which measures human organism information relating to heart beat, pulse and number of steps.

For example, as to an ictometer which is one kind of the organism information measuring device, there has been developed an ictometer adapted such that an ictometer main body having a detecting part which detects the heart beat and outputs a detected signal, a notifying part which notifies the detected signal by sound, and the like is mounted to a user's chest by a chest belt under a pressure-contacted state, and the heart beat and the like of the user are notified by sound (refer to Patent Document 1). With the ictometer described in the Patent Document 1, since it follows that the ictometer main body is mounted to the chest by the chest belt and it is mounted such that a clothing and the like are worn from thereon, there is a problem that the notifying sound is difficult to be heard.

Whereupon, there is one adapted such that the ictometer main body is caused to have a transmission function, by using a wristwatch having a reception function and a notification function, a heart beat information from the ictometer main body is received by the wristwatch, and the heart beat information is notified by a notifying part of the wristwatch. As a communication system in this case, there is a communication system by feeble radio waves or a communication system performing the communication by electromagnetic induction by using burst transmission waves.

In the communication system using the feeble radio waves, when the heart beat is notified by sound in a reception side from a received heart beat data, it scarcely undergoes influences of a noise owing to a sound notifying circuit and the like, but there are a problem that a volume in a reception side such as integrated circuit (IC) for radio, controlling IC which controls the former and antenna is large, and a problem that an electric power consumption becomes very large, and further there is a problem that it becomes expensive.

On the other hand, in the communication system using the electromagnetic induction, since portions necessary for the communication are only a coil and a waveform forming circuit, there are advantages that, in comparison with the feeble radio waves system, the volume and the electric power consumption are small, and further it becomes inexpensive.

However, since a general sound notifying circuit is constituted so as to drive a step-up coil and a piezoelectric buzzer, which have been connected in parallel, by a transistor and, at a sound notifying time, the noise emitted from the step-up coil in the sound notifying circuit interferes with the electromagnetic induction at a communication time, there is a problem that an accurate sound notification or an accurate heart beat reception cannot been performed.

Further, in the electromagnetic induction system, there are problems that it is weak against disturbance, there becomes necessary a filter by such a software as to judge whether or not the received data is truly the heart beat by a measuring time between the heart beats and the like, a program is complicated and difficult as well, and it becomes large scale one.

Further, not limited to the ictometer, in the organism information measuring device, such as pulsimeter and pedometer, which measures the organism information, in a case where a transmission/reception of the data is performed by the electromagnetic induction system and the notification is performed, there have been problems similar to the above.

<Patent Document 1> JP-UM-A-7-17202 Gazette

The present invention is one made in order to solve the above problems, and its subject is to prevent an interference between a data reception operation and a notification operation from generating in the organism information measuring device of the electromagnetic induction system.

SUMMARY OF THE INVENTION

According to the present invention, there is provided an organism information measuring device having an organism information detecting means which detects a cyclically generating organism information, a reception means which receives the organism information detected by the organism information detecting means by electromagnetic induction, and a notification means which performs a notification while synchronizing with the organism information by the reception means, characterized by possessing a control means which stops a reception operation of the reception means for a predetermined period less than a cycle in which the organism information generates and which controls, while the reception means is stopping the reception operation, the notification means so as to notify a reception of the organism information. The control means stops the reception operation of the reception means for the predetermined period less than the cycle in which the organism information generates and controls, while the reception means is stopping the reception operation, the notification means so as to perform a notification while synchronizing with the organism information.

Here, it may be constituted such that the control means calculates an average time of the cycle of the organism information received by the reception means, is constituted by having a calculation means which calculates a predetermined rate of the average time as a notification time, and controls the notification means such that it performs a notification for the notification time calculated by the calculation means.

Further, it may be constituted such that the organism information detecting means detects a heart beat or a pulse as the organism information, the calculation means calculates a time of a predetermined rate of an average heart beat time or an average pulse time as the notification time, and the control means controls the notification means such that it performs a notification for the notification time.

Further, it may be constituted such that the control means performs a control such that a time during which the reception operation of the reception means is stopped and the notification time of the notification means become the same.

Further, it may be constituted such that the organism information detecting means transmits the organism information to the reception means by the electromagnetic induction by using a burst signal.

Further, it may be constituted such that the organism information detecting means detects a heart beat, a pulse or a walk as the organism information.

BRIEF DESCRIPTION OF THE DRAWINGS

A preferred form of the present invention is illustrated in the accompanying drawings in which:

FIG. 6 is a timing diagram showing operations in the embodiment of the present invention.

DETAILED DESCRIPTION OF THE PREFERRED EMBODIMENTS

Hereunder, it is explained about an organism information measuring device concerning an embodiment of the present invention. Incidentally, in the present embodiment, an example of the ictometer is explained as the organism information measuring device.

Figure 1:
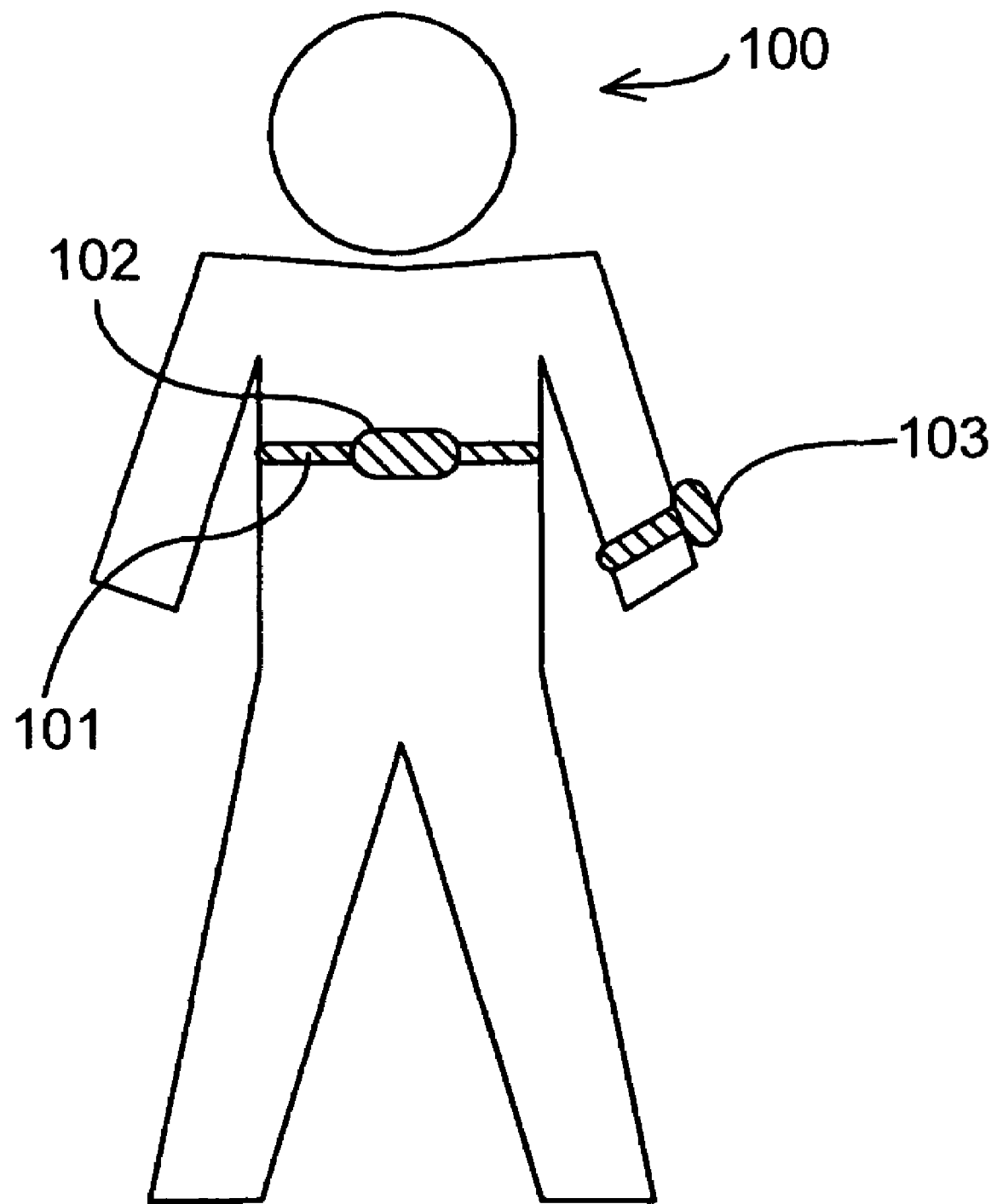
FIG. 1 is a view showing a use mode of an ictometer concerning an embodiment of the present invention.

FIG. 1 is a view showing a use mode of the ictometer concerning the present embodiment. In FIG. 1, a chest belt 101 in which a heart beat detecting part 102 has been monolithically provided is mounted to a chest of a user 100 of the ictometer, who is also a person whose heart beat is to be measured, so as to contact with his/her skin. Further, a heart beat notifying part 103 having a wristwatch function is mounted to a wrist of the user 100. The heart beat detecting part 102 and the heart beat notifying part 103 are constituted such that the transmission/reception of a signal is possible by electromagnetic induction. Incidentally, the heart beat detecting part 102 constitutes an organism information detecting means.

Although a detailed operation of the ictometer is mentioned later, a heart beat information detected by the heart beat detecting part 102 is transmitted to the heart beat notifying part 103 by electromagnetic induction, and the heart beat notifying part 103 performs a processing such as calculation of average heart beat time on the basis of the received heart beat information and performs a display, a notification and the like of the average heart beat time and the like.

Figure 2:
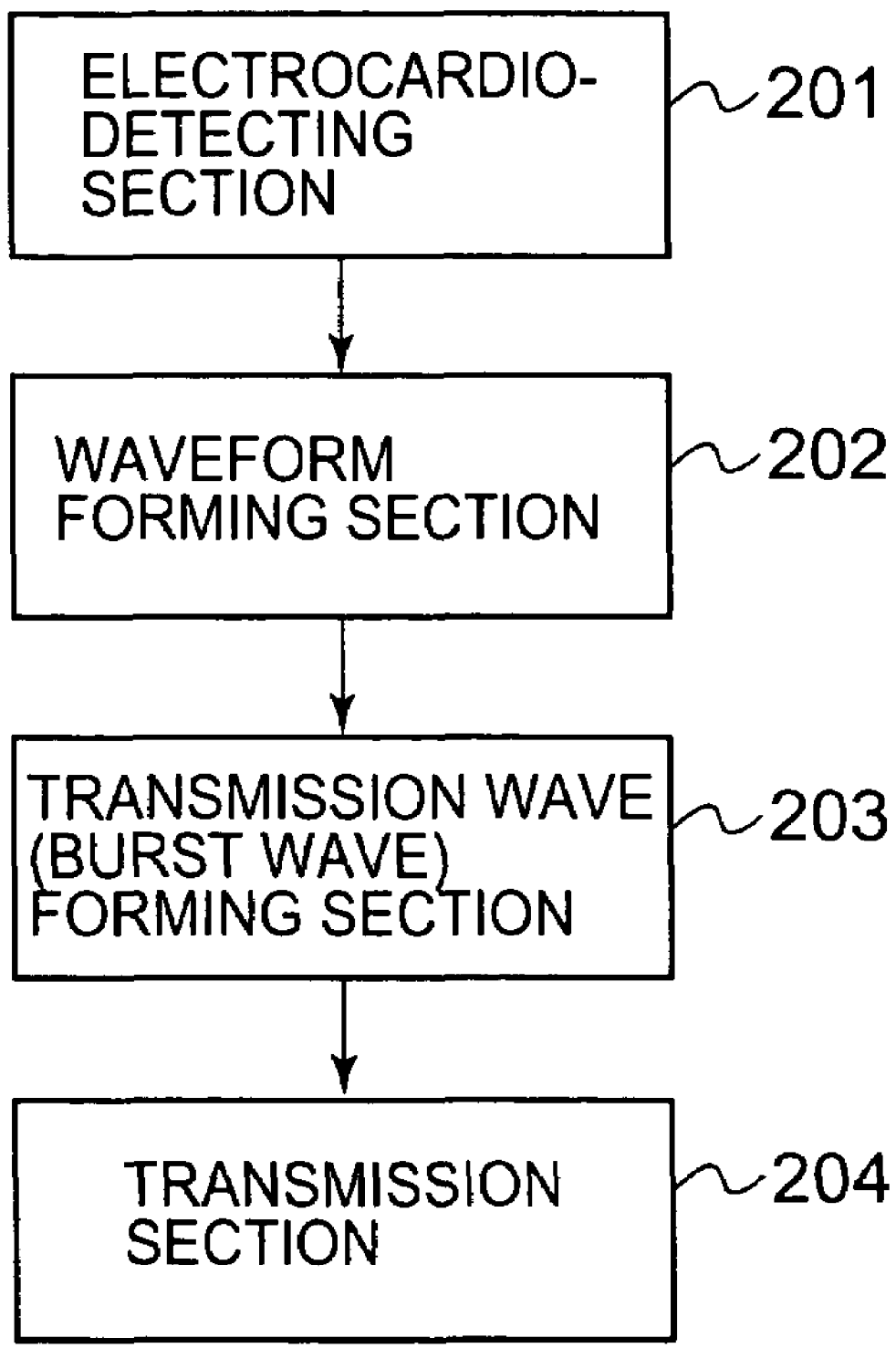
FIG. 2 is a block diagram of a heart beat detecting part used in the embodiment of the present invention.

FIG. 2 is a block diagram of the heart beat detecting part 102. In FIG. 2, the heart beat detecting part 102 possesses an electrocardio-detecting section 201 which detects the heart beat and outputs a detected signal corresponding to the heart beat, a waveform forming section 202 which amplifies the detected signal from the electrocardio-detecting section 201 and waveform-forms it to a rectangular wave, a transmission wave forming section 203 which converts the detected signal having been waveform-formed by the waveform forming section 202 into a burst signal, and a transmission section 204 which transmits the detected signal of the burst signal type from the transmission wave forming section 203 to the notifying part 103 by electromagnetic induction.

Figure 3:
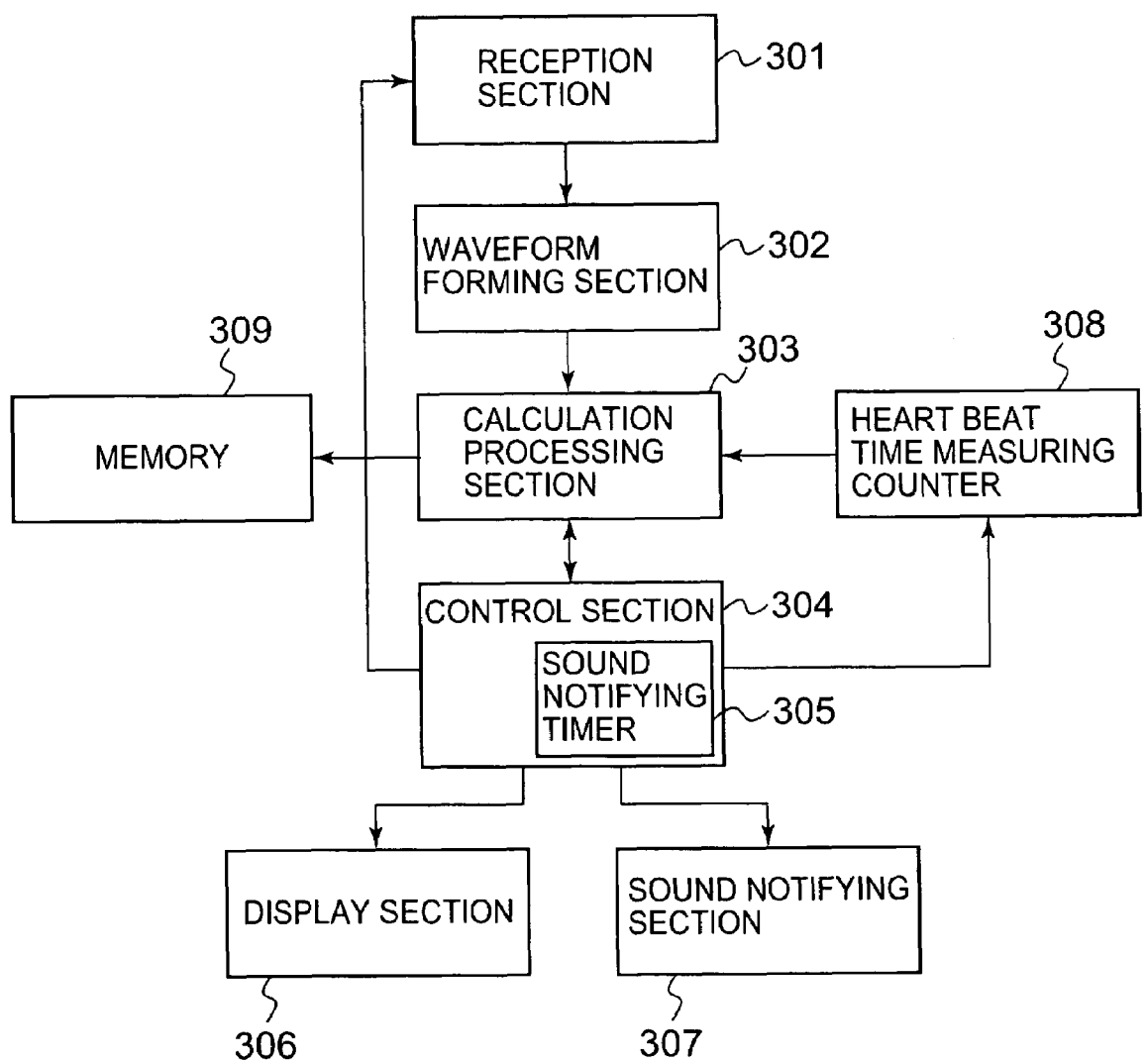
FIG. 3 is a block diagram of a notifying part used in the embodiment of the present invention.

FIG. 3 is a block diagram of the notifying part 103. In FIG. 3, the notifying part 103 possesses a reception section 301 as a reception means which receives the detected signal of the burst signal type from the heart beat detecting part 102 by the electromagnetic induction, a waveform forming section 302 which waveform-forms the detected signal of the burst signal type received by the reception section 301 to a rectangular wave signal, a calculation processing section 303 as a calculation means which calculates an average heart beat time and the like on the basis of the detected signal having been waveform-formed by the waveform forming section 302, a control section 304 which has a sound notifying timer 305 and controls each constituent element of the notifying part 103, a display section 306 as a display means displaying the average heart beat time and the like, a sound notifying section 307 as a sound notifying means performing the notification by sound, a heart beat time measuring counter 308 which measures the heart beat time of each heart beat, and a memory 309 as a storage means storing the heart beat time and the like. Incidentally, the calculation processing section 303, the control section 304, the sound notifying timer 305, and the heart beat time measuring counter 308 constitute a control means.

The sound notifying section 307 is one of the same constitution as the sound notifying circuit explained in the column of prior art, and constituted so as to drive the step-up coil and the piezoelectric buzzer, which have been connected in parallel, by the transistor.

One part of the reception section 301, the calculation processing section 303, the control section 304, the sound notifying timer 305, and the heart beat time measuring counter 308 can be constituted by a central processing unit (CPU) and, by the fact that the CPU implements a program previously stored in the memory 309, processings mentioned later are performed. FIG. 3 is one in which functions realized by the above CPU have been represented by the block diagram.

Figure 4:
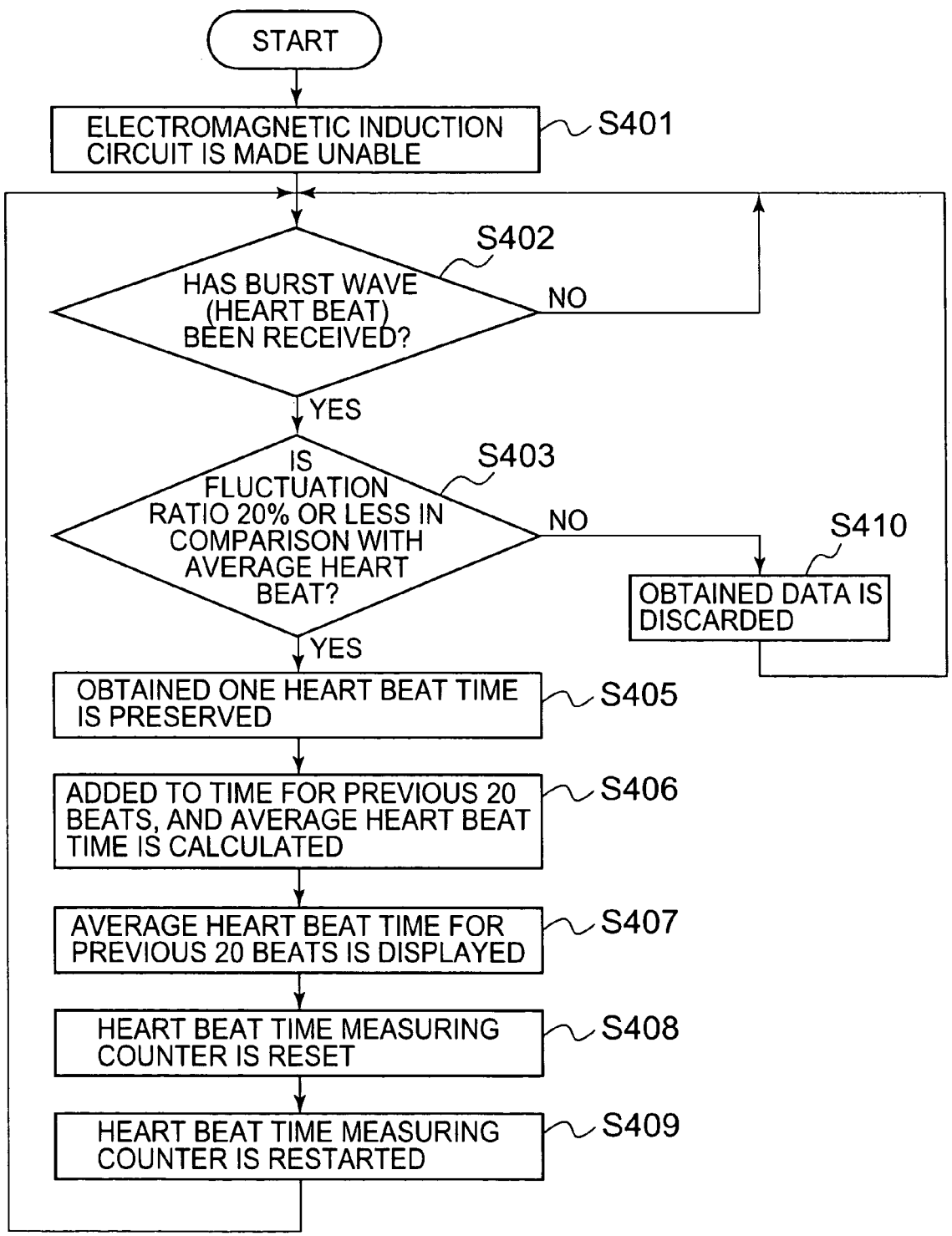
FIG. 4 is a flowchart showing processings in the embodiment of the present invention.

FIG. 4 is a flowchart representing processings in the notifying part 103, and a flowchart when performing a processing in which the detected signal of the burst signal type is received from the heart beat detecting part 102 by the electromagnetic induction, and the average heart beat time is calculated and displayed.

Figure 5:
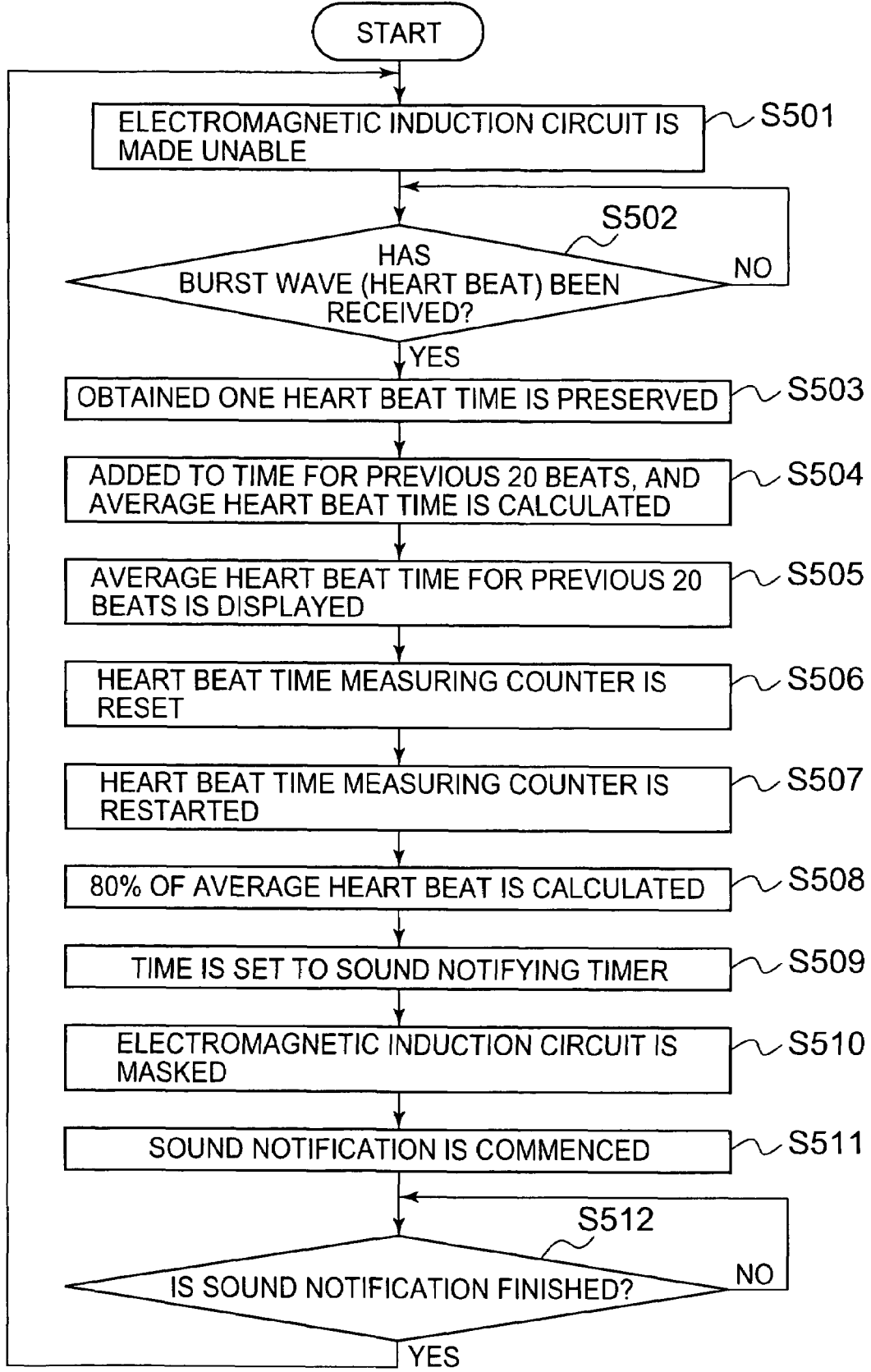
FIG. 5 is a flowchart showing processings in the embodiment of the present invention.

FIG. 5 is a flowchart representing processings in the notifying part 103, and a flowchart when performing the notification.

FIGS. 6A-6C are timing diagrams representing operations in the ictometer concerning the present embodiment.

Hereunder, the operations of the ictometer concerning the present embodiment are detailedly explained by using FIG. 1-FIG. 6C.

First, there is explained an operation when calculating and displaying an average (average heart beat time) of the heart beat time which is a time interval of the heart beat.

As shown in FIG. 2, the electrocardio-detecting section 201 of the heart beat notifying part 102 outputs the detected signal corresponding to each heart beat every time the heart beat is detected. The waveform forming section 202 amplifies the detected signal from the electrocardio-detecting section 201, and outputs it while being waveform-formed to the rectangular wave. The transmission wave forming section 203 converts the detected signal having been waveform-formed by the waveform forming section 202 into the burst signal and outputs it. The transmission section 204 transmits the detected signal of the burst signal type from the transmission wave forming section 203 to the notifying part 103 by the electromagnetic induction.

In the notifying part 103, first the control section 304 makes an electromagnetic induction circuit contained in the reception section 301 unable, and the reception section 301 is made into a state capable of receiving the detected signal from the heart beat detecting part by the electromagnetic induction (step S401 in FIG. 4). At this time, as a processing for making the reception section 301 into a reception possible state, a power source is supplied to the reception section 301 for instance.

Next, the reception section 301 judges whether or not the detected signal of the burst signal type has been received (step S402) and, in a case where it has been judged that it has been received, the waveform forming section 302 waveform-forms the detected signal to the rectangular wave, thereafter the calculation processing section 303 calculates the time interval (heart beat time) between the detected signal having been received in this time and the detected signal having been received in a previous time, compares it with a recent average heart beat time having been stored in the memory 309, and judges whether or not a fluctuation ratio of the heart beat time in this time with respect to the above average heart beat time is 20% or less (step S403).

In a case where the calculation processing section 303 has judged, in the step S403, that the fluctuation ratio is not 20% or less, the data of the heart beat time obtained in this time is discarded, and it returns to the step 402. By this, the noise is eliminated.

In a case where the calculation processing section 303 has judged, in the step S403, that the fluctuation ratio is 20% or less, it is judged that the signal is the detected signal corresponding to the heart beat and, after a data of one heart beat time obtained in this time has been preserved in the memory 309 (step S405), it calculates the average heart beat time by adding the data to the heart beat time for recent 20 beats stored in the memory 309 and dividing it by the heart beat number (step S406).

Next, the control section 304 controls the display section 306, thereby displaying the above average heart beat time to the display section 306 (step S407).

Next, the control section 304 resets the heart beat time measuring counter 308 (step S408), thereafter restarts the heart beat time measuring counter 308 (step S409), and it returns to the step S402. The heart beat time measuring counter 308 newly commences a measurement of the heart beat time from the restarting time, and the measured heart beat time concerned is used in the step S403 and the like.

By the above processings, it follows that the average heart beat time of the recent predetermined heart beat number is displayed to the display section 305 at any time.

Next, an operation when the notifying part 103 performs the notification of the heart beat information by sound is explained.

If the heart beat detecting part 102 transmits the detected signal of the burst signal type to the notifying part 103 by the electromagnetic induction in such a manner as mentioned above (refer to FIG. 6(a)), in the notifying part 103, by the fact that first the control section 304 makes the electromagnetic induction circuit contained in the reception section 301 unable, there is brought about a state that the detected signal from the heart beat detecting part 102 can be received by the reception section 301 by the electromagnetic induction (step S501 in FIG. 5), thereby commencing a reception of the detected signal from the heart beat detecting part 102. As a processing for making the reception section 301 into the reception possible state, there is a power source supply to the reception section 301 for instance.

Next, the reception section 301 judges whether or not the detected signal of the burst signal type has been received (step S502) and, in a case where it has been judged that it has been received, it is waveform-formed by the waveform forming section 302 (refer to FIG. 6(c)). Thereafter, the calculation processing section 303 calculates a time (heart beat time) between the detected signal received in this time and the detected signal received in previous time, and preserves a data of the heart beat time obtained in this time to the memory 309 (step S503).

Next, the calculation processing section 303 calculates the average heart beat time by adding the heart beat time obtained in this time to the heart beat time for recent 20 beats stored before in the memory 309 and dividing it by the heart beat number (step S504).

Next, the control section 304 controls the display section 306, thereby displaying the above average heart beat time to the display section 306 (step S505).

Next, the control section 304 resets the heart beat time measuring counter 308 (step S506), and thereafter restarts the heart beat time measuring counter 308 (step S507). The heart beat time measuring counter 308 newly commences the measurement of the heart beat time from the restarting time, and the measured heart beat time concerned is used in the step S503 and the like.

Next, the calculation processing section 303 calculates a time of predetermined rate (time of 80% in the present embodiment) of the average heart beat time within the average heart beat time calculated in the step S504 (step S508).

The control section 304 sets the time of 80% of above average heart beat time to the sound notifying timer 305 (step S509), and stops a reception operation of the reception section 301 by stopping an operation of the electromagnetic induction circuit (step S510). As a processing for stopping the reception operation of the reception section 301, there is a stop of the power source supply to the reception section 301 for instance. Further, at the same time, the control section 304 controls the sound notifying section 307, thereby commencing the notification by sound from the sound notifying section 307 (step S511).

Under this state, the control section 304 judges whether or not the sound notifying timer 305 has timed the time of 80% of the above average heart beat time, i.e., whether or not the sound notification is finished (step S512) and, if it is judged that the sound notifying timer 305 has timed the time of 80% of the above average heart beat time, it returns to the step S501 while causing the sound notifying section 307 to stop the sound notification, and the above processings are repeated.

By this, as shown in FIGS. 6A-6C, the sound notifying section 307 notifies by sound by the time of 80% of the average value of one heart beat time at a timing synchronizing with each heart beat. While this notification is being performed, since the reception operation of the reception section 301 is stopped, it becomes possible to prevent a notification operation and a reception operation of the heart beat from interfering. Further, between the heart beats, since the notification is performed by sound by the time of 80% of the recent average heart beat time, if the average value changes, the user can know also the fact that the heart beat time changes, so that the user roughly knows a value or fluctuation of the heart beat information only by sound. Further, even in a case where a noise exists in an interval of each heart beat, since the reception operation of the reception section 301 is stopped in this interval, it becomes possible to mask the noise, so that a highly accurate heart beat measurement becomes possible without undergoing an influence of the noise.

Incidentally, it may be constituted so as to detect a pulse or a walk as the above organism information and, in this case, the sound notifying section 307 is constituted so as to perform the sound notification by a time of predetermined rate of an average pulse time of the pulse, which is an average of recent pulse cycles, or an average walk time which is an average of recent walk cycles.

According to the present invention, it becomes possible to prevent a generation of the interference due to the fact that a notification operation and a data transmission/reception operation overlap. Accordingly, a highly accurate measurement of the organism information becomes possible.

Further, since the reception operation is stopped during a notification time, it becomes possible to mask the noise generated during the notification time.

Further, there is brought about an advantage that, by the fact that the predetermined rate of the average time of the cycle of the organism information is made the notification time, the user can roughly know a value and a fluctuation of the organism information only by sound.

It is applicable to an organism information measuring device, such as pulsimeter and pedometer, which measures the organism information which cyclically occurs, such as human heart beat, pulse and walk, not limited to the ictometer.

What is claimed is:

1. An organism information measuring device comprising:
   organism information detecting means for detecting organism information that is generated cyclically;
   reception means for receiving by electromagnetic induction the organism information detected by the organism information detecting means;
   notification means for notifying that the organism information detected by the organism information detecting means has been received by the reception means; and
   control means for controlling the notification means to stop a reception operation of the reception means for a predetermined period less than a cycle in which the organism information is generated and to notify a reception of the organism information detected by the organism information detecting means while the reception operation of the reception means is stopped.

2. An organism information measuring device according to claim 1; wherein the control means calculates an average time of the cycle of the organism information received by the reception means, the control means including calculation means for calculating a rate of the average time of the received organism information as a notification time and for controlling the notification means to notify the reception of the organism information for a period of time corresponding to the notification time calculated by the calculation means.

3. An organism information measuring device according to claim 2; wherein the organism information detected by the organism information detecting means comprises one of heart beat information and pulse information, and the rate of the average time calculated as a notification time by the calculation means comprises one of an average heart rate time and an average pulse time, respectively; and wherein the control means controls the notification means to notify the reception of the heart beat information or the pulse information for a period of time corresponding to the notification time calculated by the calculation means.

4. An organism information measuring device according to claim 2; wherein the control means controls the notification means such that a time during which the reception operation of the reception means is stopped and the notification time of the notification means become the same.

5. An organism information measuring device according to claim 1; wherein the organism information detecting means transmits the organism information to the reception means by electromagnetic induction using a burst signal.

6. An organism information measuring device according to claim 1; wherein the organism information detected by the organism information detecting means comprises one of a heart beat and a pulse.

7. An organism information measuring device according to claim 1; wherein the notification means generates electromagnetic noise during notification of the reception of the organism information; and wherein the control means controls the notification means to notify the reception of the organism information detected by the organism information detecting means while the reception operation of the reception means is stopped, so that interference between electromagnetic noise generated by the notification means and an electromagnetic induction signal transmitted by the organism information detecting means is prevented.

8. An organism information measuring device according to claim 7; wherein the organism information detecting means transmits the organism information to the reception means by electromagnetic induction using a burst signal.

9. An organism information measuring device according to claim 7; wherein the organism information detected by the organism information detecting means comprises one of a heart beat and a pulse.

10. An organism information measuring device according to claim 7; wherein the control means calculates an average time of the cycle of the organism information received by the reception means, the control means including calculation means for calculating a rate of the average time of the received organism information as a notification time and for controlling the notification means to notify the reception of the organism information for a period of time corresponding to the notification time calculated by the calculation means.

11. An organism information measuring device according to claim 10; wherein the organism information detected by the organism information detecting means comprises one of heart beat information and pulse information, and the rate of the average time calculated as a notification time by the calculation means comprises one of an average heart rate time and an average pulse time, respectively; and wherein the control means controls the notification means to notify the reception of the heart beat information or the pulse information for a period of time corresponding to the notification time calculated by the calculation means.

12. An organism information measuring device according to claim 10; wherein the control means controls the notification means such that a time during which the reception operation of the reception means is stopped and the notification time of the notification means become the same.

13. An organism information measuring device comprising:
   a reception unit that receives organism information generated cyclically;
   a detection unit that detects and transmits the organism information to the reception unit by electromagnetic induction;
   a notification unit that provides notification of receipt of the organism information by the reception unit while generating electromagnetic noise; and
   a control circuit that controls the reception unit to stop a reception operation for a predetermined period less than a cycle in which the organism information is generated and that controls the notification unit to provide notification of receipt by the reception unit of the organism information transmitted by the detection unit while the reception operation of the reception unit is stopped, so that interference between electromagnetic noise generated by the notification unit and an electromagnetic induction signal transmitted by the detection unit is prevented.

14. An organism information measuring device according to claim 13; wherein the detection unit transmits the organism information to the reception unit by electromagnetic induction using a burst signal.

15. An organism information measuring device according to claim 13; wherein the organism information detected by the detection unit comprises one of a heartbeat and a pulse.

16. An organism information measuring device according to claim 13; wherein the control circuit calculates an average time of the cycle of the organism information received by the reception unit; and wherein the control circuit includes a calculation circuit that calculates a rate of the average time of the received organism information as a notification time and that controls the notification unit to notify the reception of the organism information for a period of time corresponding to the calculated notification time.

17. An organism information measuring device according to claim 16; wherein the organism information detected by the detection unit comprises one of heartbeat information and pulse information, and the rate of the average time calculated as a notification time by the calculation circuit comprises one of an average heart rate time and an average pulse time, respectively; and wherein the control circuit controls the notification unit to notify the reception of the heartbeat information or the pulse information for a period of time corresponding to the notification time calculated by the calculation circuit.

18. An organism information measuring device according to claim 16; wherein the control circuit controls the notification unit such that a time during which the reception operation of the reception unit is stopped and the notification time of the notification unit become the same.

19. An organism information measuring device comprising:

a reception unit that receives organism information generated cyclically;

a detection unit that detects and transmits the organism information to the reception unit by electromagnetic induction;

a notification unit that provides notification of receipt of the organism information by the reception unit; and a control circuit that controls the reception unit to stop a reception operation for a predetermined time interval and that controls the notification unit to provide notification of receipt by the reception unit of the organism information transmitted by the detection unit during the time interval.

20. An organism information measuring device according to claim 19; wherein the notification unit generates electromagnetic noise during notification of the reception by the reception unit of the organism information transmitted by the detection unit; and wherein the control circuit controls the notification unit to notify the reception of the organism information during the time interval so that interference between electromagnetic noise generated by the notification unit and an electromagnetic induction signal transmitted by the detection unit is prevented.

21. An organism information measuring device according to claim 19; wherein the organism information comprises heartbeat information; and wherein the predetermined time interval is a period of time corresponding to 80% of an average heart beat time.

22. An organism information measuring device according to claim 19; wherein the organism information comprises heartbeat information; and wherein during the time interval, the control circuit controls the notification unit to perform notification of heartbeat in synchronization with each heart beat.

23. An organism information measuring device according to claim 22; wherein the control circuit controls the notification unit to perform notification of the heartbeat by sound.

* * * * *